United States Patent
Young

(10) Patent No.: US 7,704,690 B2
(45) Date of Patent: Apr. 27, 2010

(54) SYNTHESIS OF ERROR-MINIMIZED NUCLEIC ACID MOLECULES

(75) Inventor: Lei Young, Rockville, MD (US)

(73) Assignee: Synthetic Genomic, Inc., La Jolla, CA (US)

( * ) Notice: Subject to any disclaimer, the term of this patent is extended or adjusted under 35 U.S.C. 154(b) by 0 days.

(21) Appl. No.: 11/633,686

(22) Filed: Dec. 4, 2006

(65) Prior Publication Data

US 2007/0128649 A1 Jun. 7, 2007

Related U.S. Application Data

(60) Provisional application No. 60/741,469, filed on Dec. 2, 2005.

(51) Int. Cl.
C12Q 1/68 (2006.01)
C12P 19/34 (2006.01)

(52) U.S. Cl. .................. 435/6; 435/91.1; 435/91.2

(58) Field of Classification Search .............. None
See application file for complete search history.

(56) References Cited

U.S. PATENT DOCUMENTS

| | | | | |
|---|---|---|---|---|
| 6,165,793 | A * | 12/2000 | Stemmer | 435/440 |
| 2003/0148283 | A1 | 8/2003 | Barany et al. | |
| 2003/0207292 | A1 | 11/2003 | Notomi et al. | |
| 2004/0023327 | A1 | 2/2004 | Short et al. | |
| 2005/0106590 | A1 | 5/2005 | Lathrop et al. | |
| 2005/0255477 | A1 | 11/2005 | Carr et al. | |
| 2006/0127926 | A1* | 6/2006 | Belshaw et al. | 435/6 |
| 2007/0196834 | A1* | 8/2007 | Cerrina et al. | 435/6 |

OTHER PUBLICATIONS

Miyazaki et al., "Random/DNA fragmentation with endonuclease V: application to DNA shuffling," Nucleic Acids Research, 2002, vol. 30, No. 24, pp. 1-3.*
Fuhrmann et al., "Removal of mismatched bases from synthetic genes by enzymatic cleavage," Nucleic acids Research, Mar. 2005, vol. 33, No. 6, e58, 1-8.*
Binkowski, B.F. et al., "Correcting errors in synthetic DNA through consensus shuffling," Nucleic Acids Research, Mar. 1, 2005, vol. 33, No. 6, Oxford University Press.
Richmond, K.E. et al., "Amplification and assembly of chip-eluted DNA (AACED): a method for high-throughput gene synthesis," Nucleic Acids Research, Aug. 9, 2004, pp. 5011-5018, vol. 32, No. 17, Oxford University Press.
Tian, J. et al., "Accurate multiplex gene synthesis from programmable DNA microchips," Nature, Dec. 2004, pp. 1050-1054, vol. 432, Nature Publishing Group.
Young, L. et al., "Two-step total gene synthesis method," Nucleic Acids Research, Mar. 19, 2004, vol. 32, No. 7, Oxford University Press.
Liang et al., Biochemistry (2004) 43(42):13459-13466.
Reid, In Vitro Cell. Dev. Biol. Plant (2000) 36(5):331-337.
Stemmer, PNAS USA (1994) 91:10747-10751.
Supplementary European Search Report for EP 06844856.2, mailed Feb. 12, 2009, 10 pages.
International Preliminary Report on Patentability for PCT/US2006/046457, issued Jun. 4, 2008, 6 pages.

* cited by examiner

Primary Examiner—Young J Kim
(74) Attorney, Agent, or Firm—Morrison & Foerster LLP

(57) ABSTRACT

A method is provided for synthesis of error-minimized nucleic acid molecules. Oligonucleotides intended to have fragments of a desired, full-length nucleotide sequence, and optionally containing other desired nucleotides, such as nucleotides for binding the oligonucleotides to a substrate, are obtained. Oligonucleotides for both strands of the desired, full-length sequence may be obtained. The oligonucleotides are amplified and assembled into a first set of molecules intended to have the desired, full-length nucleotide sequence. The first set of molecules is denatured and annealed to form a second set of molecules intended to have the desired, full-length nucleotide sequence. The second set of molecules is cut into smaller segments, for example, by mixing the molecules with endonucleases that form blunt cuts in the second set of molecules where there are sequence errors, as well as randomly along the molecules. The smaller segments are assembled into a set of molecules intended to have the desired, full-length nucleotide sequence. By promoting cutting of the molecules in this manner near the end of the nucleic acid molecule synthesis process, a set of full-length molecules can be obtained with fewer nucleotide sequence errors than can be achieved with other methods.

20 Claims, 3 Drawing Sheets

SYNTHESIS OF ERROR-MINIMIZED NUCLEIC ACID MOLECULES

CROSS-REFERENCE TO RELATED APPLICATIONS

The present application claims benefit and priority from U.S. Provisional Patent Application Ser. No. 60/741,469 filed on Dec. 2, 2005, entitled, "Error Correction Method."

BACKGROUND OF THE INVENTION

1. Field of the Invention

The present invention relates generally to molecular biology, and more particularly to the synthesis of genes and other nucleic acid molecules.

2. Description of Related Art

To test hypotheses in the field of genomics, and to synthesize designed proteins and organisms with tailored genomes, cost-effective methods for synthesizing nucleic acid molecules with a high degree of fidelity to an intended nucleotide sequence are required. Recently, efforts to synthesize genes accurately while controlling costs have yielded methods including microchip-based gene synthesis and PCR-based gene assembly technologies. While these conventional technologies provide the capability to synthesize multiple genes, reducing errors introduced into the desired gene-sequence remains challenging. To avoid the problems with sequence errors inherent in gene synthesis, some have focused on purifying the oligonucleotides that are used at the early stages of the synthesis process. However, these oligonucleotide purification approaches are costly, and sequence errors persist and propagate through the subsequent steps of the synthesis process.

What is desired is a way to synthesize genes and other nucleic acid molecules with a greater yield of molecules having a desired nucleotide sequence. An approach that can correct sequence errors at a much later step in the synthesis process makes the desired increase in nucleotide sequence accuracy possible, while allowing the process to be cost-effective.

SUMMARY OF THE INVENTION

A method is provided for nucleic acid molecule synthesis with error correction. Synthesis of a molecule having a desired, full-length nucleotide sequence generally begins with oligonucleotides intended to have fragments of the desired, full-length nucleotide sequence, and optionally containing other desired nucleotides, such as nucleotides for binding the oligonucleotides to a substrate. The oligonucleotides may be synthesized for both strands of the desired, full-length sequence, increasing the efficiency of oligonucleotide use in the synthesis and thus controlling its cost. The oligonucleotides are amplified, and assembled into a first set of molecules intended to have the desired, full-length nucleotide sequence. It may be ensured that the oligonucleotides are grouped according to their nucleotide sequence, to improve the fidelity of assembled molecules to the desired nucleotide sequence. Molecules in the first set are denatured and annealed to form a second set of molecules intended to have the desired, full-length nucleotide sequence. Molecules in the second set are cut into smaller segments, for example, by mixing the molecules with endonucleases that form blunt cuts in the second set of molecules where there are sequence errors, as well as randomly along the molecules in the second set. The smaller segments are assembled into a set of molecules intended to have the desired, full-length nucleotide sequence. By promoting cutting of the molecules in this manner near the end of the nucleic acid molecule synthesis process, a set of full-length molecules may be obtained with fewer nucleotide sequence errors than can be obtained with prior art methods.

DETAILED DESCRIPTION OF THE INVENTION

Figure 1:
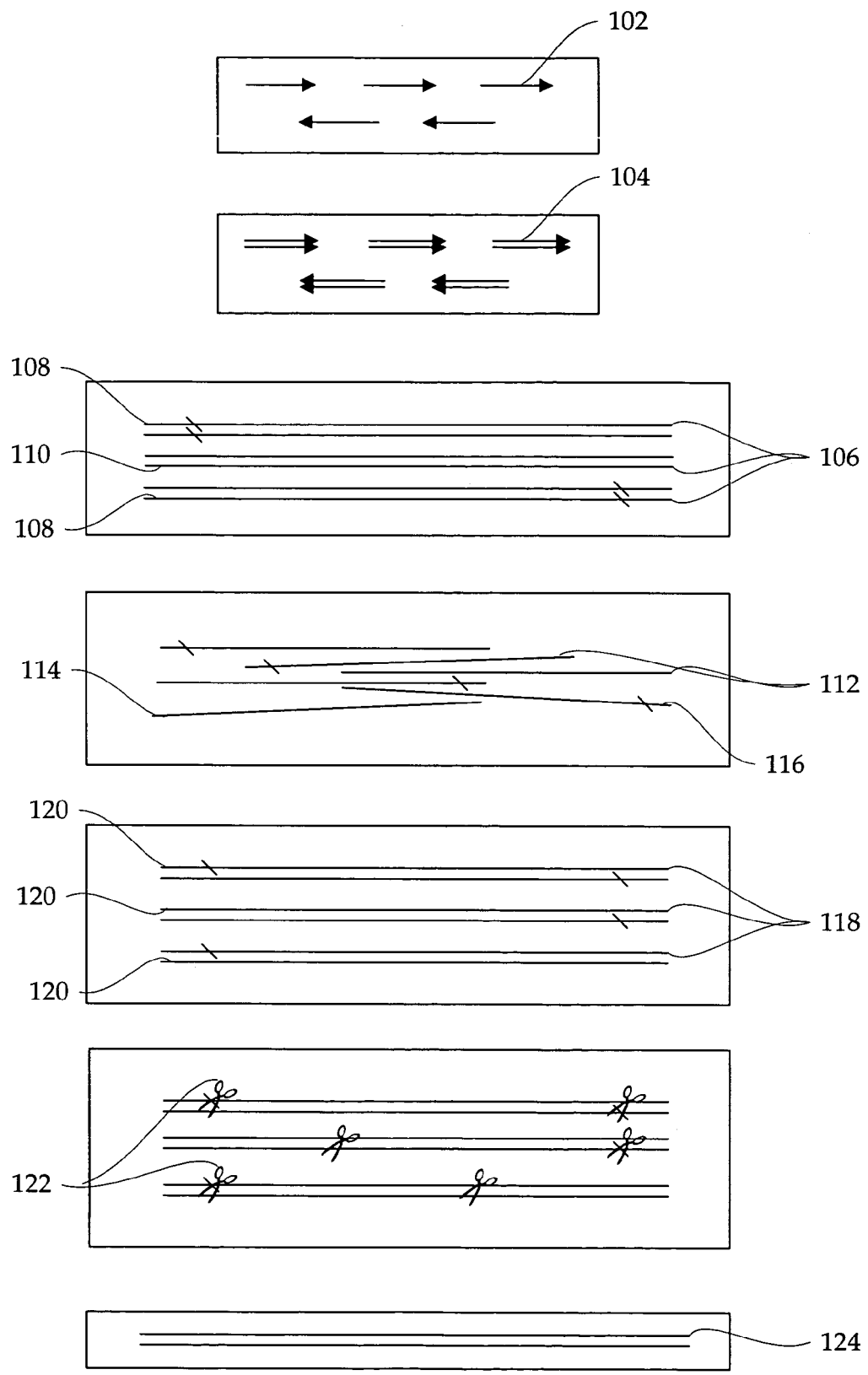
FIG. 1 is a diagram showing various stages in an exemplary method for synthesis of error-minimized nucleic acid molecules.

Synthesizing nucleic acid molecules with a nucleotide sequence that falls within a range of desired sequences is a persistent challenge in the fields of molecular biology and genomics. Over the past several decades, a great deal of research effort has been directed to synthesizing error-minimized nucleic acid molecules. Methods providing significant reductions in nucleotide sequence errors, and/or increases in synthesis efficiency or reduction in cost, enable progress in basic biomedical and bioengineering research and improve the productivity of the biotechnology industry. Prior art approaches to these problems include purification of oligonucleotides by various means.

Embodiments or methods of the present invention provide a process for synthesizing error-minimized nucleic acid molecules. An "error" is a deviation from the desired nucleotide sequence that the nucleic acid molecules are intended to have. Errors include deletions from, substitutions in, and additions to the desired nucleotide sequence, and may arise at any point in the synthesis by any mechanism. Nucleic acid molecules include DNAs (deoxyribonucleic acids), RNAs (ribonucleic acids), and PNAs (protein-nucleic acids) from any source or combination of sources, with or without modifications. Nucleic acid molecules of any length and geometry (e.g., circular, linear) that can allow the provided reactions to proceed fall within the scope of the invention. Modifications include changes in one or more nucleotide, sugar, and/or phosphate moieties of the nucleic acid molecules, as well as the substitution of one or more naturally occurring molecular features with one or more synthetic features. For example, a base (i.e., a nucleotide such as adenine) may be substituted with a biotinylated base. Any modification or modifications that can allow the provided reactions to proceed fall within the scope of the invention. One of skill in the art will appreciate the applicability of the provided method to a wide variety of problems, including synthesizing error-minimized genes or genomes, and synthesizing DNA fragments for use in recombinant DNA technology.

Oligonucleotide fragments ("oligos") intended to have a desired nucleotide sequence for an experimental or other purpose are obtained. Oligos are single-stranded nucleic acid molecules intended to include a portion of the nucleotide sequence desired for one strand of a double-stranded nucleic acid molecule. Oligos may be obtained in any manner, e.g., by purchase from commercial sources, or by synthesis using any conventional method, including automated synthesis. In a preferred embodiment, to improve the efficiency and reduce the cost of nucleic acid molecule synthesis, one or more sets of oligos intended to have the desired nucleotide sequence for both strands of a double-stranded nucleic acid molecule (rather than for only a single strand of the nucleic acid molecule) are obtained. Oligos may be affixed to a substrate, such as a DNA chip.

The oligos are "amplified," i.e., their quantities are increased. Methods for amplifying oligos are well known, such as conventional PCR (polymerase chain reaction) amplification. Nucleotide sequence error analysis may also be performed. Methods for nucleotide sequence error analysis are well known, such as sequencing, DNA chip methods, and hybridization methods.

The oligos are then assembled into larger nucleic acid molecules, again using well-known techniques such as overlap-extension PCR. In a preferred embodiment, it is ensured that the amplified oligos are separated into groups that are considered to form the same fragment of nucleotide sequences before they are assembled into larger nucleic acid molecules. In some embodiments, this separation may be accomplished based on the presence of adaptor primers at an end of each oligo, wherein the adaptor primer for each oligo intended to have a desired nucleotide sequence is itself unique. In other embodiments, oligos having different nucleotide sequences are synthesized in enough quantity and mixed in separate test tubes, so that no additional separation is required before their assembly into larger nucleic acid molecules. Ensuring separation as here provided increases control over the assembly of larger nucleic acid molecules, resulting in improved ability to synthesize error-minimized nucleic acid molecules.

The assembled nucleic acid molecules are double-stranded by default. Double-stranded nucleic acid molecules are then denatured and annealed by conventional methods. For example, heat denaturation of double-stranded nucleic acid molecules separates the double-stranded molecules into pairs of corresponding single-stranded molecules. Cooling the single-stranded molecules promotes their annealing into double-stranded molecules as individual the nucleotides comprising the nucleic acid molecules coalesce into nucleotide base pairs along complementary stretches of nucleotide sequence. The kinetics or other physical or chemical parameters of denaturation and annealing may be controlled to promote mixing of the single-stranded molecules, so that the single-stranded molecules change partners. For example, if a double-stranded DNA molecule had a sequence error in both strands at the $400^{th}$ nucleotide from one end, after denaturation and annealing, the single strands of that molecule may be paired with other single-stranded molecules lacking an error at that position. Thus, the denaturation and annealing process can produce double-stranded nucleic acid molecules with mismatches between nucleotide bases at sites of error. These mismatches can be targeted for removal, for example, by reacting annealed molecules with endonucleases under appropriate conditions.

An aspect of the invention may be practiced to reduce errors in double-stranded nucleic acid molecules. A first set of double-stranded nucleic acid molecules, which are intended to have a desired nucleotide sequence and a desired length, are reacted with one or more endonucleases. Under appropriate conditions, the endonucleases cut the nucleic acids into smaller fragments. These fragments are then assembled into a second set of double-stranded nucleic acid molecules, which are intended to have a desired nucleotide sequence and a desired length. In a preferred embodiment, the first set of molecules is reacted with T7 endonuclease I, E. coli endonuclease V, and Mung Bean endonuclease in a buffer containing manganese. In this instance, the endonucleases are intended to introduce blunt cuts in the molecules wherever there is a sequence error, as well as randomly at error-free sites. When such cuts are accomplished, the result is shorter, double-stranded molecules that each contain an error-free fragment of his desired full-length nucleotide sequence. Conventional methods are used to assemble these fragments into a second set of double-stranded nucleic acid molecules, which are overwhelmingly more likely to have the desired nucleotide sequence and desired length than were the first set of molecules.

FIG. 1 is a diagram showing various stages in an exemplary method for synthesis of error-minimized nucleic acid molecules. Oligonucleotide fragments ("oligos") 102 are used to synthesize longer molecules. The longer molecules are intended to have a desired nucleotide sequence of a desired length. The desired length may also be called the "full length," and may be the length of the entire desired nucleotide sequence. For example, a naturally occurring gene for the protein arrestin may have a sequence of 2178 deoxyribonucleic acid base pairs. The gene being synthesized may be intended to have a specific sequence of 2178 base pairs. The desired length of the gene to be synthesized would then be 2178 base pairs, which is the full length of the desired nucleotide sequence. Optionally, an additional nucleotide sequence may be introduced to the 2178 base pairs, for example, to add one or more non-expressed regulatory regions to the naturally occurring gene. In another embodiment, one or more base pairs of the naturally occurring nucleotide sequence may be deleted, for example, to remove some non-expressed nucleotides, or to experiment with the structure of the expressed protein. The full length of the molecule intended to have a desired nucleotide sequence may be determined in any manner.

The desired nucleotide sequence may comprise a naturally occurring gene sequence, a nucleotide sequence designed by man with or without computer assistance, a hybrid of naturally occurring and manmade nucleotide sequences, or an altered naturally occurring gene sequence. The desirability of a nucleotide sequence may be determined by the amino acid sequence of its translation product, that is, of the protein that is produced when the gene is expressed. For example, a desired nucleotide sequence for producing arrestin by expressing a synthesized arrestin gene of 2178 base pairs need not be perfectly identical to a published, deduced, naturally occurring gene sequence for arrestin, as long as the deviations from that gene sequence result in the production of the same protein. In an alternative example, the desirability of a nucleotide sequence may be determined by the presence of a non-expressed nucleotide sequence that may have a regulatory role in gene transcription. The desirability of a nucleotide sequence may be determined by any experimental purpose or other intention.

Each oligo 102 is intended to have a desired nucleotide sequence that includes a fragment of the full-length desired nucleotide sequence. For example, an oligo used to synthesize a gene with a full length of 1000 base pairs may have a length of 50 base pairs. Each arrow representing an oligo 102 denotes a group of one or more molecules intended to have a desired nucleotide sequence. For example, an oligo 102 may comprise molecules that are 50 base pairs in length and contain the nucleic acid sequence "ATGATC," coding for the amino acids methionine and isoleucine, as well as molecules that are 50 base pairs in length and contain the nucleic acid sequence "ATGATT," which also code for methionine and isoleucine, despite the difference in the nucleotide sequence at the position of the rightmost cysteine (which has been replaced by thymine). Each oligo 102 can be any number of molecules the sequences of which meet the criteria for the desired nucleotide sequence.

The diagram depicts five distinct oligos 102 for the purpose of illustration, but any number of oligos 102 may be used. The oligos 102 may be obtained in any manner, including purchase from an industrial supplier and/or independent synthesis. Any number of oligos 102 may be obtained in a manner different from that in which one or more other oligos 102 are obtained. For example, some oligos 102 may be purchased, obtained as a gift, or synthesized by any method. Any oligo 102 may or may not be sequenced to determine whether it comprises enough molecules with the desired nucleotide sequence. Any of the oligos 102 may optionally be further purified to reduce the number of any nucleotide-sequence errors they may bear.

In some embodiments, the oligos 102 are obtained for both strands of the nucleic acid molecule that is intended to have a desired nucleotide sequence. In the prior art, oligos 102 are obtained for only a single strand of DNA that is intended to have a desired nucleotide sequence. Oligos 102 may be obtained for both strands of DNA so that a set of oligos 102 comprises some oligos 102 having overlapping fragments of a full-length desired nucleotide sequence. A set of oligos 102 with such sequence overlaps can be used to assemble a full-length molecule intended to have a desired nucleotide sequence more efficiently than is possible using the approaches in the prior art. This increase in efficiency means that a smaller amount of, or no, full-length molecules intended to have a desired nucleotide sequence may be used in order to obtain more full-length molecules intended to have a desired nucleotide sequence. This unprecedented efficiency allows better control of the costs of nucleic acid molecule synthesis.

The oligos 102 are amplified into the oligos 104, increasing the number of molecules comprising each oligo 102. Each amplified oligo 104 is represented by a double arrow. The double arrow is merely a representational device: the number of molecules of each oligo 104 after amplification is not necessarily twice the number of molecules of each oligo 102 present before amplification, and is likely orders of magnitude greater. Any amplified oligo 104 may or may not be sequenced to determine whether it comprises enough molecules with the desired nucleotide sequence. Any amplified oligo 104 optionally may be further purified to reduce the number of any nucleotide-sequence errors they may bear.

The amplified oligos 104 are used to assemble a first set of full-length molecules 106 that are intended to have a desired nucleotide sequence. Double, parallel line-segments represent a full-length, double-stranded DNA molecule 106. Within a set of such full-length molecules 106, however, it is expected that there may be one or more molecules with one or more sequence errors 108. Sequence errors are denoted with a short slash along the full-length molecule 108. There may be many molecules 108 with one or more sequence errors at different points in the sequence. Within a set of such full-length molecules 106, it may also be expected that there are one or more molecules without any sequence errors 110.

The first set of full-length molecules 106 is denatured, so that the two strands of each molecule separate. The set of denatured, single-stranded, full-length molecules 112 thus may comprise one or more molecules without sequence errors 114, and one or more molecules with one or more sequence errors 116. There may be many molecules 116 with one or more sequence errors at different points in the sequence. The set of full-length molecules 106 may be denatured in any manner, for example, by heating the molecules 106.

The set of denatured molecules 112 is then annealed to obtain a second set of full-length molecules 118 that are intended to have a desired nucleotide sequence. Within a set of such full-length molecules 122, the technician may expect there to be one or more molecules with one or more sequence errors 120, and one or more molecules without any sequence errors (not shown). The denatured set of full-length molecules 112 may be annealed in any manner, for example, by cooling the molecules 112.

There may be many molecules 120 with one or more sequence errors at different points in the sequence. The distribution of sequence errors over the second set of molecules 118 will most likely be different from that over the first set of molecules 106, since one or more single-stranded molecules 114 and 116 will anneal to other single-stranded molecules 114 and 116 different from those to which they were bound before denaturation. For example, a double-stranded molecule 108 in the first set of molecules 106 may have two sequence errors, one in each strand, that are directly across from each other. During denaturation, a single strand 116 from the molecule 108 may move near a single-stranded molecule without errors 114. During annealing, a second full-length molecule 120 may form that has an error in only one of its two strands.

The second set of full-length molecules 118 may be cut to form a third set of molecules (not shown), so that two or more molecules in the third set of molecules are shorter than full-length molecules 106 or 118. In some embodiments, cuts 122 are intended to occur wherever there is a sequence error in either or both strands. Cuts 122 may also be intended to occur where there is no sequence error. The cuts 122 may be blunt cuts. The set of cuts 122 may be achieved in any manner. For example, one or more endonucleases may be added to the second set of full-length molecules 118 to cut them into a third set of molecules (not shown).

In an exemplary embodiment, the molecules 118 are mixed with three endonucleases in a buffer. For instance, the molecules 118 may be mixed with T7 endonuclease I, *E. coli* endonuclease V, and Mung Bean endonuclease in a buffer that contains manganese. In this instance, the endonucleases may be intended to introduce blunt cuts in the molecules 118 at the sites of any sequence errors, as well as at random sites where there is no sequence error, obtaining a third set of molecules comprising at least two molecules that are shorter than a full-length molecule.

The third set of molecules is assembled into a fourth set of full-length molecules 124. In an exemplary embodiment described above, the set of cuts 122 eliminated sequence errors from the second set of molecules 118. Thus, the number of sequence errors in the set of molecules 124 is much lower than that in the set of molecules 118. By providing a unique and powerful error-correction process operating late in the nucleic acid molecule synthesis process, the exemplary method for synthesis of error-minimized nucleic acid molecules yields a set of full-length molecules 124 intended to have a desired nucleotide sequence that has remarkably fewer errors than can be obtained using gene synthesis methods in the prior art.

Figure 2:
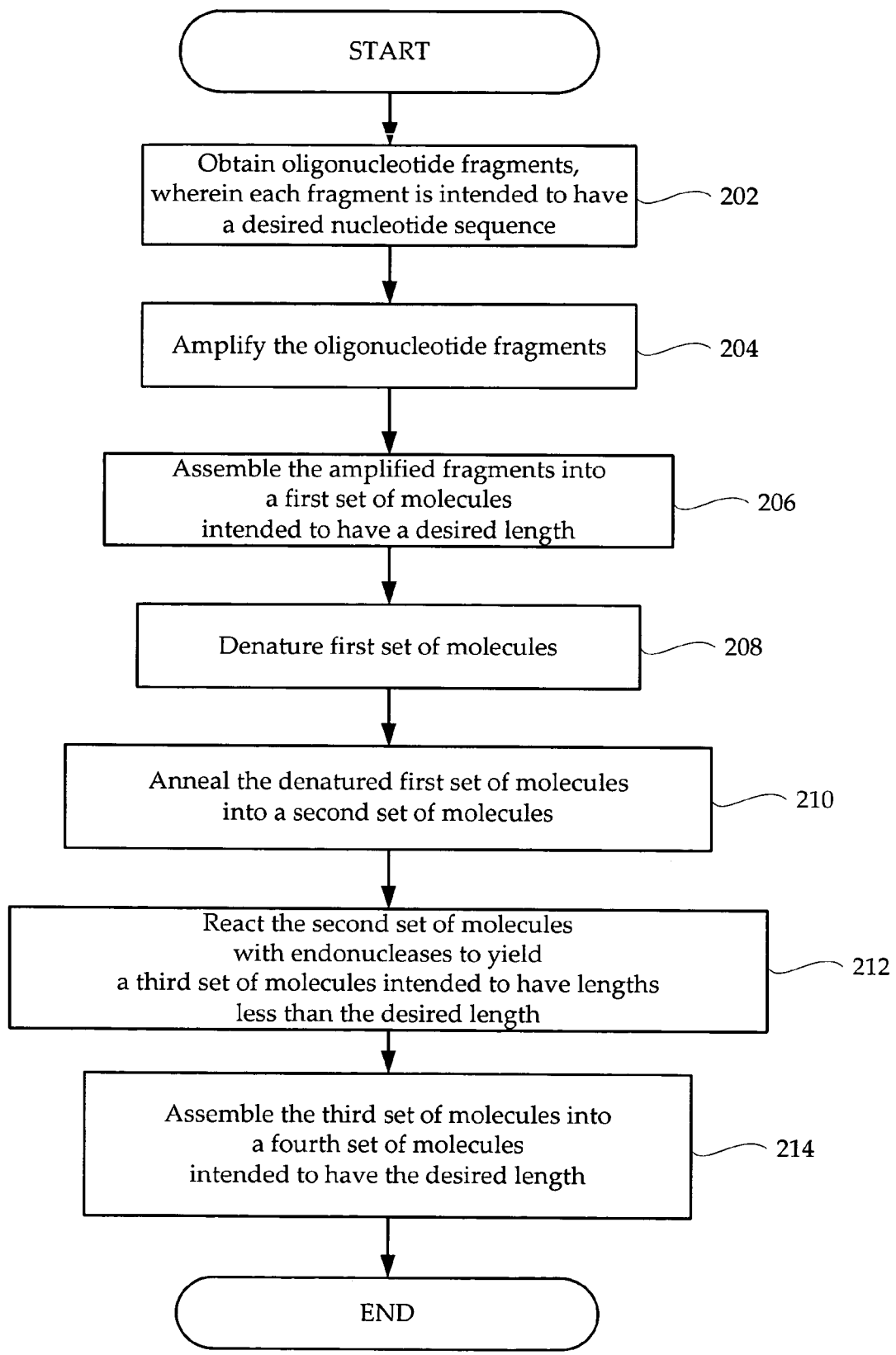
FIG. 2 is a flow chart of an exemplary process for synthesis of error-minimized nucleic acid molecules.

FIG. 2 is a flow chart of an exemplary process for synthesis of error-minimized nucleic acid molecules. At step 202, oligos 102 (FIG. 1) of a length smaller than that of the full-length desired nucleotide sequence (i.e., "oligonucleotide fragments" of the full-length desired nucleotide sequence) are obtained. Each oligo 102 is intended to have a desired nucleotide sequence that comprises a part of the full length desired nucleotide sequence. Each oligo 102 may also be intended to have a desired nucleotide sequence that comprises an adapter primer for PCR amplification of the oligo 102, a tethering sequence for attachment of the oligo 102 to a DNA microchip, or any other nucleotide sequence determined by any experimental purpose or other intention. The oligos 102 may be obtained in any of one or more ways, for example, through synthesis, purchase, etc.

At step 204, the oligos 102 are amplified to obtain more of each oligo 102. The amplification may be accomplished by any method, for example, by PCR. Introduction of additional errors into the nucleotide sequences of any of the oligos 102 may occur during amplification. The distinct amplified oligos 104 (FIG. 1) result from the amplification at step 204. Oligos 102 may be amplified by adapter primers, and the adapter sequence may be cleaved off by means of type IIS restriction endonucleases.

At step 206 the amplified oligos are assembled into a first set of molecules 106 (FIG. 1) intended to have a desired length, which is the full length of the desired nucleotide sequence that the technician intends to synthesize. Assembly of amplified oligos 104 into full-length molecules 106 may be accomplished in any way, for example, by using a PCR-based method. One or more of the full-length molecules 106 may be a molecule containing nucleotide sequence errors in one or both of its strands 108 (FIG. 1). One or more of the full-length molecules 106 may be a molecule containing no nucleotide sequence errors 110 (FIG. 1).

At step 208 the first set of full-length molecules 106 are denatured. Denaturation renders single-stranded molecules 112 (FIG. 1) from double-stranded molecules 106. Denaturation may be accomplished by any means. In some embodiments, denaturation is accomplished by heating the molecules 106. One or more of the single-stranded molecules 112 may be a molecule without nucleotide sequence errors 114 (FIG. 1). One or more of the single-stranded molecules 112 may be a molecule containing nucleotide sequence errors 116 (FIG. 1).

At step 210 the denatured molecules 112 are annealed. Annealing renders a second set of full-length, double-stranded molecules 118 from single-stranded molecules 112. Annealing may be accomplished by any means. In some embodiments, annealing is accomplished by cooling the molecules 112. One or more of the double-stranded molecules 118 (FIG. 1) may be a molecule containing nucleotide sequence errors 120 (FIG. 1). One or more of the double-stranded molecules 118 may be a molecule without nucleotide sequence errors.

At step 212 the second set of full-length molecules 118 are reacted with one or more endonucleases to yield a third set of molecules intended to have lengths less than the length of the complete desired gene sequence. The endonucleases cut one or more of the molecules in the second set into shorter molecules. The cuts 122 (FIG. 1) may be accomplished by any means. Cuts 122 at the sites of any nucleotide sequence errors are particularly desirable, in that assembly of pieces of one or more molecules that have been cut at error sites offers the possibility of removal of the cut errors at step 214.

In an exemplary embodiment, the molecules 118 are cut with T7 endonuclease I, *E. coli* endonuclease V, and Mung Bean endonuclease in the presence of manganese. In this embodiment, the endonucleases are intended to introduce blunt cuts in the molecules 118 at the sites of any sequence errors, as well as at random sites where there is no sequence error.

At step 214, the third set of molecules is assembled into a fourth set of molecules 124 (FIG. 1), whose length is intended to be the full length of the desired nucleotide sequence. Because of the late-stage error correction enabled by the provided method, the set of molecules 124 is expected to have many fewer nucleotide sequence errors than can be provided by methods in the prior art.

Figure 3:
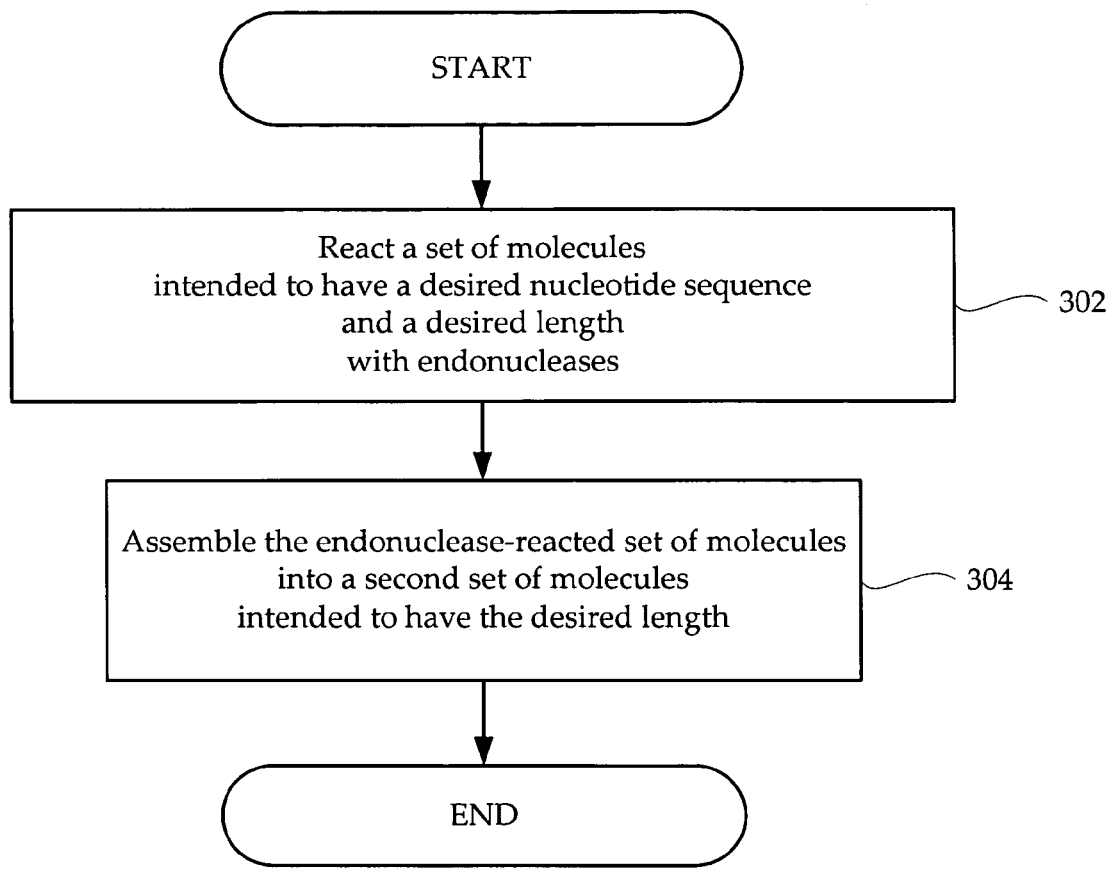
FIG. 3 is a flow chart of an exemplary process for nucleic acid molecule sequence error correction.

FIG. 3 is a diagram of an exemplary process for DNA sequence error correction. At step 302 a set of molecules intended to have a desired nucleotide sequence and a desired length is reacted with endonucleases. The endonucleases cut one or more of the molecules into shorter molecules. Cuts at the sites of any nucleotide sequence errors are particularly desirable, in that assembly of pieces of one or more molecules that have been cut at error sites offers the possibility of removal of the cut errors at step 304.

At step 304, the endonuclease-reacted molecules are assembled into a second set of molecules, the lengths of which are intended to be the full length of the desired nucleotide sequence. Because of the error correction enabled by the provided method, the second set of molecules is expected to have remarkably fewer nucleotide sequence errors than can be provided by methods in the prior art.

If for any reason it is desired to perform additional error correction on the set of molecules 124 (FIG. 1), the molecules 124 may be subjected to the error correction method disclosed in U.S. Provisional Patent Application Ser. No. 60/741,469 filed on Dec. 2, 2005, which is herein incorporated by reference.

According to one exemplary method, the following reaction conditions are appropriate to obtain a desired result. Overlapping oligos approximately sixty nucleotides in length ("60 mer") are synthesized. These oligos overlap each other by approximately 17 bp at the 3' end, and 43 bp at the 5' end. All oligos are mixed together, (up to 1.2 kb final length) in a final concentration of 50 nM, in 1× Phusion GC buffer and 1 Unit of Phusion polymerase for every 20 microL. PCA conditions are: 96 C 10 s, 52 C 20 s, 72 C 20 s for 5 cycles, then 98 C 15 s, 62 C 20 s, 72 C 1 min for 30 cycles. Target DNA fragments are then amplified by the terminal 2 primers by Phusion polymerase, using 1 microL of the PCA reaction as a template in 20 microL final volume, with conditions of: 98 C 15 s, 62 C 20 s, 72 C 1 min for 30 cycles. The PCR products are gel purified and diluted to 10 ng/microL in 10 mM Tris-Cl, 50 mM NaCl, 2 mM MnCl2, 1 mM DTT, pH 7.9. The mixture is denatured at 95 C for 5 min, then annealed at 68 C for 30 min. 1 unit each of T7 endonuclease I, *E. coli* endonuclease V and Mung Bean nuclease are added per 20 microL reaction, and incubated at 37 C for 1.5 hr, the 60 C 5 min, 37 C 1 s for 15 cycles. 1 microL of the error correction product are used in a second PCA-PCR synthesis procedure, with the conditions for both PCA and PCR of: 98 C 15 s, 62 C 20 s, 72 C 1 min for 30 cycles.

In another example, 90 mer oligos have one adapter sequence, and the strands complementary to the adapter primer are synthesized (as compared to both strands). In the amplification step, the adapter primer first extends to the end of these complementary strands, then finds the other newly extended complementary strand. The amplified fragment contains 120 bp of gene specific sequence, and overlaps each other by 45 bp, which allows more efficient overlap extension.

For instance, 4000 oligos, each 90 bases long and each containing one adapter primer sequence, are synthesized on a microfluidic chip, and cleaved off to form oligomix. Every 40 oligos are amplified by a different set of adapter primers in a separate test tube or similar reaction vessel. The amplification reaction (50 microL) comprises 2 microM each of the adapter primer, 200 microM each dNTP, 1 unit of Phusion polymerase and 100 ng of oligomix. The adapter primers contain BseRI restriction sites, so the gene specific fragments are released from the adapter sequences. The released fragments are gel purified and subjected to PCA (no primers). The PCA conditions are: 96 C 10 s, 52 C 20 s, 72 C 20s for 5 cycles, then 98 C 15 s, 62 C 20 s, 72 C 1 min for 30 cycles. The target DNA fragments are amplified by the terminal 2 primers by Phusion polymerase using 1 microL of the PCA reaction as template in 20 micoL final volume, with the conditions of: 98 C 15 s, 62 C 20 s, 72 C 1 min for 30 cycles. Amplified fragments may then be subjected to one or more of the error correction steps described herein.

In a further example for synthesizing longer fragments, sequential 3'->5' exonuclease and exonuclease assembly reactions may be performed. For instance, 2 µg total of 2 kb fragments, overlapping each other by at least 100 bp, are mixed in 30 mM Tris-HCl, pH 8.0 @ 25° C, 4 mM MgCl2, 26 µM NAD, 50 mM NaCl, 200 µM each dNTP, 1 mM Dithiothreitol, 50 µg/ml BSA, and chewed back with 200 Units of exonuclease III for 2 to 10 minutes. The reaction is then immediately or near immediately incubated at 72° C. for 15 min and cooled to 30° C. T7 single strand binding protein (ssb) is added to 2 µM and incubated at 30° C. for 15 min, then 200 U/mL of E. coli ligase and 50 U/mL of E. coli polymerase I are added to repair the gaps at 30° C. for 15 min. 50 U/mL of T5 exonuclease is added and the reaction is incubated at 30° C. for 30 min. A circular assembled molecule results, with all, or most all, of the unassembled fragments degraded.

While various embodiments have been described above, it should be understood that they have been presented by way of example only, and not limitation. For example, any other set of endonuclease reaction components and conditions that achieves the provided method may be used. Thus, the breadth and scope of a preferred embodiment should not be limited by any of the above-described exemplary embodiments.

What is claimed is:

1. A method for error correction with nucleic acid molecule synthesis, the method comprising:
    (a) obtaining oligonucleotide fragments, each intended to have a portion of a desired nucleotide sequence, of a desired length;
    (b) amplifying the oligonucleotide fragments;
    (c) assembling the amplified fragments into a first set of molecules intended to have the desired length;
    (d) denaturing the first set of molecules;
    (e) annealing the denatured molecules into a second set of molecules intended to have the desired length;
    (f) reacting the second set of molecules with a plurality of endonucleases, thereby introducing blunt cuts in the second set of molecules at sites of sequence error, yielding a third set of molecules containing fragments less than the desired length, wherein the plurality of endonucleases is intended to cut at sites of any sequence error; and
    (g) assembling the third set of molecules containing fragments into a fourth set of molecules of the desired length, whereby the number of errors in the fourth set of molecules is reduced as compared to the first set of molecules.

2. The method of claim 1, wherein the desired nucleotide sequence comprises one or more naturally occurring gene sequences.

3. The method of claim 1, wherein the desired nucleotide sequence comprises one or more synthetic nucleotide sequences.

4. The method of claim 1, wherein the desired nucleotide sequence comprises a hybrid of one or more naturally occurring gene sequences and one or more synthetic nucleotide sequences.

5. The method of claim 1, wherein obtaining the oligonucleotide fragments comprises synthesizing the fragments.

6. The method of claim 5, wherein obtaining the oligonucleotide fragments comprises synthesizing fragments on a microchip.

7. The method of claim 1, wherein obtaining the oligonucleotide fragments comprises synthesizing a set of fragments that is intended to have portions of both strands of the desired nucleotide sequence.

8. The method of claim 1, further comprising grouping the oligonucleotide fragments of step (b) according to the sequences of the fragments before they are assembled.

9. The method of claim 1, wherein the oligonucleotides are obtained and kept in separate containers prior to amplification, wherein each group of fragments that shares a unique sequence is kept in separate container.

10. The method of claim 8, wherein grouping the amplified oligonucleotide fragments comprises using unique adaptor primers.

11. The method of claim 1, wherein assembling the amplified fragments into the first set of molecules or assembling the third set of molecules into a fourth set of molecules comprises using overlap-extension polymerase chain reaction.

12. The method of claim 1, further comprising processing the fourth set of molecules with one or more rounds of additional error correction.

13. The method of claim 1, further comprising amplifying the fourth set of molecules by one or more polymerase chain reactions.

14. The method of claim 1, further comprising cloning the fourth set of molecules into one or more vectors.

15. The method of claim 1, further comprising sequencing the fourth set of molecules.

16. The method of claim 1, wherein the plurality of endonucleases comprises T7 endonuclease I.

17. The method of claim 1, wherein the plurality of endonucleases comprises three endonucleases.

18. The method of claim 17, wherein the plurality of endonucleases comprises Mung Bean endonuclease, T7 endonuclease I, and E. coli endonuclease V.

19. The method of claim 1, wherein the reacting in step (f) is carried out in the presence of manganese.

20. The method of claim 1, wherein reaction with the plurality of endonucleases cuts molecules in the second set both at sites of sequence error and randomly, at error-free sites.

* * * * *